(12) United States Patent
Mainkar et al.

(10) Patent No.: US 11,488,705 B2
(45) Date of Patent: *Nov. 1, 2022

(54) HEAD MODELING FOR A THERAPEUTIC OR DIAGNOSTIC PROCEDURE

(71) Applicant: Neuronetics, Inc., Malvern, PA (US)

(72) Inventors: Neeraj Mainkar, Minneapolis, MN (US); Ravi Pillutla, Audubon, PA (US); Kenneth Marc Ghiron, Malvern, PA (US); Mark Edward Riehl, Doylestown, PA (US)

(73) Assignee: Neuronetics, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/843,997

(22) Filed: Apr. 9, 2020

(65) Prior Publication Data
US 2020/0251203 A1    Aug. 6, 2020

Related U.S. Application Data

(63) Continuation of application No. 16/297,119, filed on Mar. 8, 2019, now Pat. No. 10,636,520, which is a
(Continued)

(51) Int. Cl.
*G06F 19/00* (2018.01)
*G16H 30/20* (2018.01)
(Continued)

(52) U.S. Cl.
CPC .............. *G16H 30/20* (2018.01); *G06K 9/00* (2013.01); *G06T 17/00* (2013.01); *G16H 20/40* (2018.01);
(Continued)

(58) Field of Classification Search
CPC ........ G16H 30/20; G16H 20/40; G16H 50/20; G16H 50/50; G06K 9/00; G06K 9/00221; G06T 17/00; G06T 2210/44
See application file for complete search history.

(56) References Cited

U.S. PATENT DOCUMENTS 6,173,068 B1   1/2001  Prokoski
6,862,374 B1   3/2005  Nagai et al.
(Continued)

FOREIGN PATENT DOCUMENTS

WO    WO 2008070001 A2    6/2008

*Primary Examiner* — Sultana M Zalalee
(74) *Attorney, Agent, or Firm* — Flaster Greenberg, P.C.

(57) ABSTRACT

A model of a human subject's head may be generated to assist in a therapeutic and/or diagnostic procedure. A treatment and/or diagnostic system may generate a fitted head model using a predetermined head model and a plurality of points. The plurality of points may include facial feature information and may be determined using a sensor, for example, an IR or optical sensor. One or more anatomical landmarks may be determined and registered in association with the fitted head model using the facial feature information, for example, without the use of additional image information, such as an MRI image. The fitted head model may include visual aids, for example, anatomical landmarks, reference points, marking of the human subject's MT location, and/or marking of the human subject's treatment location. The visual aids may assist a technician to perform the therapeutic and/or diagnostic procedure of the human subject.

20 Claims, 7 Drawing Sheets

Related U.S. Application Data continuation of application No. 15/699,392, filed on Sep. 8, 2017, now Pat. No. 10,282,515, which is a continuation of application No. 14/618,407, filed on Feb. 10, 2015, now Pat. No. 9,792,406.

(60) Provisional application No. 61/937,951, filed on Feb. 10, 2014.

(51) Int. Cl.

| | | |
|---|---|---|
| *G06K 9/00* | (2022.01) | |
| *G06T 17/00* | (2006.01) | |
| *G16H 50/50* | (2018.01) | |
| *G16H 20/40* | (2018.01) | |
| *G16H 50/20* | (2018.01) | |
| *G06V 40/16* | (2022.01) | |

(52) U.S. Cl.
CPC ............. *G16H 50/20* (2018.01); *G16H 50/50* (2018.01); *G06T 2210/44* (2013.01); *G06V 40/16* (2022.01)

(56) References Cited

U.S. PATENT DOCUMENTS

| | | |
|---|---|---|
| 7,087,008 B2 | 8/2006 | Fox et al. |
| 9,792,406 B2 | 10/2017 | Mainkar et al. |
| 10,282,515 B2 | 5/2019 | Mainkar et al. |
| 10,636,520 B2* | 4/2020 | Mainkar ................ G06T 17/00 |
| 2003/0023159 A1 | 1/2003 | Tanner |
| 2003/0050527 A1* | 3/2003 | Fox ........................ A61B 34/37 600/13 |
| 2005/0113630 A1 | 5/2005 | Fox et al. |
| 2006/0052687 A1 | 3/2006 | Ruohonen |
| 2007/0232918 A1 | 10/2007 | Taylor |
| 2008/0212894 A1 | 9/2008 | Demirli et al. |
| 2008/0262565 A1 | 10/2008 | Bentwich |
| 2008/0288035 A1 | 11/2008 | Gill et al. |
| 2009/0149898 A1* | 6/2009 | Hulvershorn ...... A61N 1/36082 607/3 |
| 2009/0153552 A1 | 6/2009 | Fidaleo et al. |
| 2010/0172567 A1 | 7/2010 | Prokoski |
| 2010/0189342 A1 | 7/2010 | Parr et al. |
| 2010/0249577 A1* | 9/2010 | Schneider .............. A61N 2/006 600/424 |
| 2010/0254594 A1 | 10/2010 | Wang et al. |
| 2010/0286470 A1 | 11/2010 | Schneider et al. |
| 2011/0134240 A1* | 6/2011 | Anderson ............... H04W 4/38 348/143 |
| 2011/0172553 A1 | 7/2011 | John et al. |
| 2011/0188738 A1 | 8/2011 | Roussel |
| 2011/0207988 A1 | 8/2011 | Ruohonen et al. |
| 2011/0230710 A1 | 9/2011 | Hoeg et al. |
| 2011/0236868 A1 | 9/2011 | Bronstein et al. |
| 2011/0261225 A1 | 10/2011 | Niinami |
| 2012/0007859 A1 | 1/2012 | Lee et al. |
| 2012/0154557 A1 | 6/2012 | Perez et al. |
| 2013/0178693 A1 | 7/2013 | Neuvonen et al. |
| 2013/0339043 A1* | 12/2013 | Bakar ................... A61B 5/0205 705/2 |
| 2014/0046114 A1* | 2/2014 | Nishikawa ............... A61N 2/02 600/9 |
| 2014/0160123 A1 | 6/2014 | Yang et al. |
| 2014/0261467 A1 | 9/2014 | Zhang et al. |
| 2015/0095063 A1* | 4/2015 | Sherman ................ G16H 20/17 705/3 |
| 2020/0402284 A1* | 12/2020 | Saragih .................. G06T 17/00 |

* cited by examiner

HEAD MODELING FOR A THERAPEUTIC OR DIAGNOSTIC PROCEDURE

CROSS-REFERENCE TO RELATED APPLICATIONS

This application is a continuation of U.S. patent application Ser. No. 16/297,119, filed Mar. 8, 2019, which is a continuation of U.S. patent application Ser. No. 15/699,392, filed Sep. 8, 2017, now U.S. Pat. No. 10,282,515, issued on May 7, 2019, which is a continuation of U.S. patent application Ser. No. 14/618,407, filed Feb. 10, 2015, now U.S. Pat. No. 9,792,406, issued on Oct. 17, 2017, which claims the benefit of U.S. Provisional Application No. 61/937,951, filed Feb. 10, 2014, the disclosure of which is incorporated herein by reference in its entirety.

BACKGROUND

A number of medical ailments are treated or treatable through the application of electrical stimulation to an afflicted portion of a human subject's body. Examples of electrical stimulation may include magnetic or inductive stimulation, which may make use of a changing magnetic field, and electric or capacitive stimulation in which an electric field may be applied to the tissue. Neurons, muscle, and tissue cells are forms of biological circuitry capable of carrying electrical signals and responding to electrical stimuli. For example, when an electrical conductor is passed through a magnetic field, an electric field is induced causing current to flow in the conductor. Because various parts of the body may act as a conductor, when a changing magnetic field is applied to the portion of the body, an electric field is created causing current to flow. In the context of biological tissue, for example, the resultant flow of electric current stimulates the tissue by causing neurons in the tissue to depolarize. Also, in the context of muscles, for example, muscles associated with the stimulated neurons contract. In essence, the flow of electrical current allows the body to stimulate typical and often desired chemical reactions.

Electrical stimulation has many beneficial and therapeutic biological effects. For example, the use of magnetic stimulation is effective in rehabilitating injured or paralyzed muscle groups. Another area in which magnetic stimulation is proving effective is treatment of the spine. The spinal cord is difficult to access directly because vertebrae surround it. Magnetic stimulation may be used to block the transmission of pain via nerves in the back (e.g., those responsible for lower back pain). Further, unlike the other medical procedures that stimulate the body, electrical stimulation may be non-invasive. For example, using magnetic fields to generate current in the body produces stimulation by passing the magnetic field through the skin of a human subject.

Magnetic stimulation also has proven effective in stimulating regions of the brain, which is composed predominantly of neurological tissue. One area of particular therapeutic interest is the treatment of neuropsychiatric disorders. It is believed that more than 28 million people in the United States alone suffer from some type of neuropsychiatric disorder. These include specific conditions such as depression, schizophrenia, mania, obsessive-compulsive disorder, panic disorders, just to name a few. One particular condition, depression, is the often referred to as the "common cold" of psychiatric disorders, believed to affect 19 million people in the United States alone, and possibly 340 million people worldwide. Modern medicine offers depression human subjects a number of treatment options, including several classes of anti-depressant medications like selective serotonin reuptake inhibitors (SSRI), MAIs, tricyclics, lithium, and electroconvulsive therapy (ECT). Yet many human subjects remain without satisfactory relief from the symptoms of depression.

Repetitive transcranial magnetic stimulation (rTMS) has been shown to have anti-depressant effects for human subjects, even those that do not respond to the traditional methods and medications. For example, a subconvulsive stimulation may be applied to the prefrontal cortex in a repetitive manner, causing a depolarization of cortical neuron membranes. The membranes are depolarized by the induction of small electric fields, usually in excess of 1 volt per centimeter (V/cm). These small electric fields result from a rapidly changing magnetic field applied non-invasively.

Therapeutic and diagnostic procedures, such as TMS for example, may require a technician to locate a treatment location (e.g., or target location that is used to determine the treatment location) before performing the therapeutic and/or diagnostic procedure. This process can be time consuming and burdensome. For example, the technician may be required to manually collect multiple points on a patient one-by-one to generate a model of the patient, and after the model is generated, locate the treatment location on the model.

SUMMARY

A system for creating a model, such as a fitted head model, may be provided. The system may comprise a sensor, a processor, a memory, a transceiver, a power supply, a treatment coil, and/or a display device. The processor may be configured to determine a plurality of points associated with the human subject's head using the sensor. For example, the processor may be configured to determine a plurality of points using the sensor and without the use of an indicator tool. The sensor may comprise an infrared (IR) sensor. One or more (e.g., each) of the plurality of points that are associated with the human subject's head may comprises an x coordinate, a y coordinate, and a z coordinate in a coordinate system (e.g., Cartesian coordinate system, a cylindrical coordinate system, and/or the like). A subset of the plurality of points may comprise facial feature information relating to the human subject. The facial feature information may include information relating to a location of one or more facial features of the human subject, such as, but not limited to a nose, an eye, an ear, chin, hairline, and/or mouth of the human subject.

The processor may be configured to generate a fitted head model using a predetermined head model and the plurality of points. For example, the processor may be configured to generate the fitted head model using a cubic spline method. The processor may be configured to, for example, morph the predetermined head model to the plurality of points to generate the fitted head model. The predetermined head model may be a generic head model that does not include any characteristics that are specific to one individual. The predetermined head model may include location information relating to the one or more anatomical landmarks. An anatomical landmark may comprise a nasion, an inion, a lateral canthus, an external auditory meatus (e.g., ear attachment point), and/or one or more preauricular points of the human subject. An anatomical landmark may be associated with an x coordinate, a y coordinate, and a z coordinate of the predetermined head model. The predetermined head model may comprise predefined coordinates, for example, such as an Electroencephalography (EEG) 10-20 coordinate grid, one or more treatment locations, and/or the like.

The fitted head model may have a smooth surface. For example, the processor may be configured to determine that one or more points of the plurality of points are associated with rippling of the human subject's skin, loss of a facial feature, and/or an asymmetric lump, and generate the fitted head model without the use of the points associated with the rippling of the human subject's skin, loss of a facial feature, or asymmetric lump. The fitted head model may not include the human subject's hair. For example, the plurality of points that are used to create the fitted head model may be devoid of information relating to the human subject's hair such that the fitted head model is devoid of information relating to the human subject's hair. The processor may be configured to determine that one or more points of the plurality of points that are used to create the fitted head model are associated with the human subject's hair, and the processor may be configured to generate the fitted head model without the use of the points associated with the human subject's hair. The fitted head model may comprise an EEG 10-20 coordinate grid.

The processor may be configured to determine a location of one or more anatomical landmarks on the fitted head model using the facial feature information. For example, the processor may be configured to perform triangulation and/or trilateration using the facial feature information (e.g., one or more points associated with the facial feature information) to determine the location of one or more anatomical landmarks of the human subject on the fitted head model. An anatomical landmark may be associated with an x coordinate, a y coordinate, and a z coordinate of the fitted head model. The processor may be configured to register the anatomical landmarks with the fitted head model.

The processor may be configured to determine a target location on the fitted head model based on one or more anatomical landmarks. For example, the processor may be configured to determine a target location on the fitted head model based on one or more anatomical landmarks without the use of additional image information, for example, such as, but not limited to magnetic resonance imaging (MRI) image information, x-ray image information, and/or the like. The target location may comprise a treatment location or a reference point that may be used to determine the treatment location. The processor may be configured to display the fitted head model and the target location on the display device, for example, to assist in a therapeutic or diagnostic procedure. The processor may be configured to perform transcranial magnetic stimulation (TMS) using the fitted head model and/or the target location. The fitted head model may be saved for the human subject, for example, so that it can be recalled and used during a subsequent therapeutic or diagnostic procedure.

DETAILED DESCRIPTION

Figure 1:
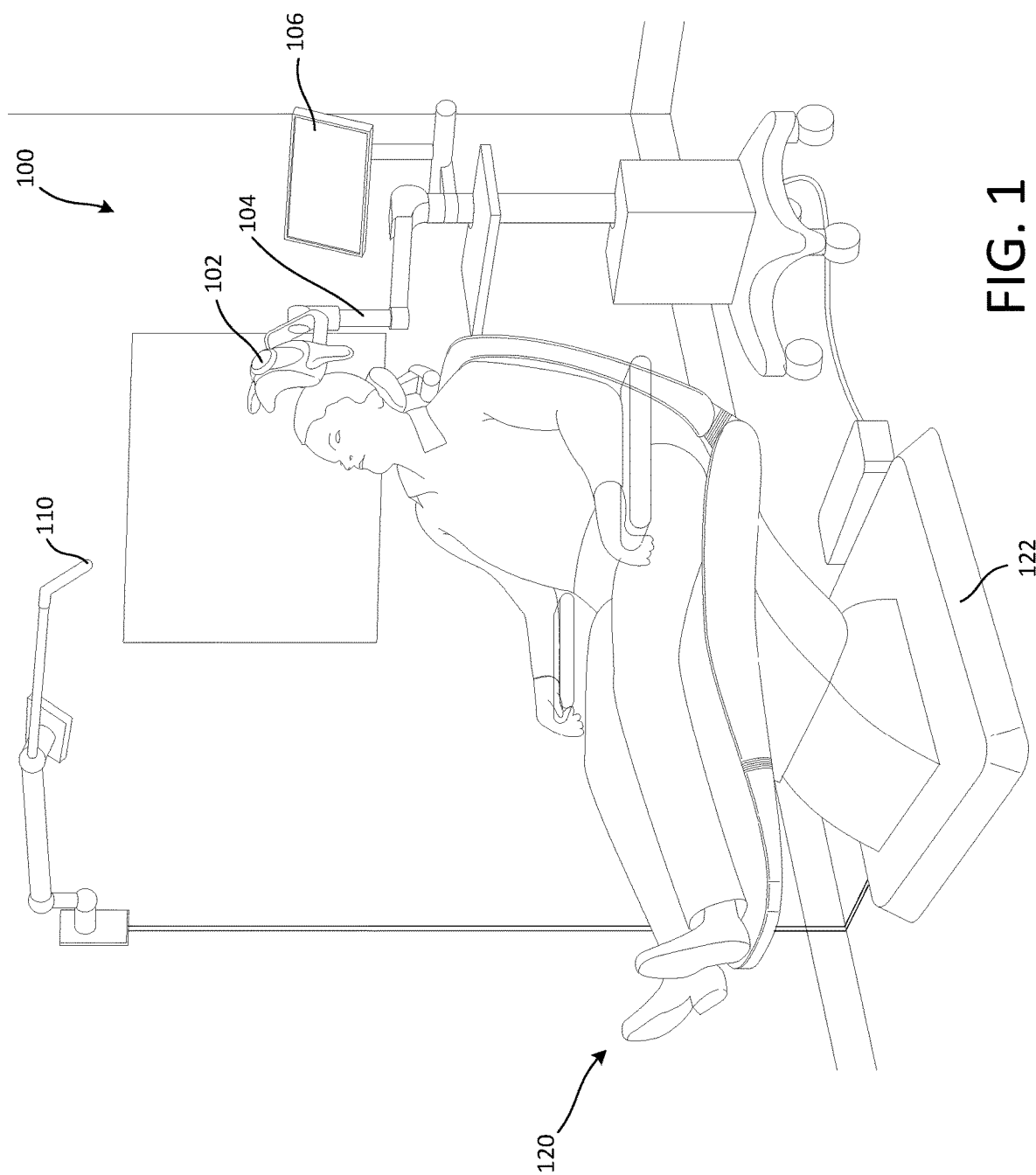
FIG. 1 is a diagram of an example of a treatment system.

A detailed description of illustrative embodiments will now be described with reference to the various Figures. Although this description provides a detailed example of possible implementations, it should be noted that the details are intended to be examples and in no way limit the scope of the application.

In 1831, Michael Faraday discovered that the magnitude of an electric field induced on a conductive loop is proportional to the rate of change of magnetic flux that cuts across the area of the conductive loop. Faraday's law may be represented as E~–(dB/dt), where E is the induced electric field in volts/meter, dB/dt is the time rate of change of magnetic flux density in Tesla/second. In other words, the amount of electric field induced in an object like a conductor may be determined by two factors: the geometry and the time rate of change of the flux. The greater the derivative of the magnetic flux, the greater the induced electric field and resulting current density. Because the magnetic flux density decreases quickly with distance from the source of the magnetic field, the flux density is greater the closer the conductor is to the source of the magnetic field. When the conductor is a coil, the current induced in the coil by the electric field may be increased in proportion to the number of turns of the coil.

When the electric field is induced in a conductor, the electric field creates a corresponding current flow in the conductor. The current flow is in the same direction of the electric field vector at a given point. The peak electric field occurs when dB/dt is the greatest and diminishes at other times. If the magnetic field changes, for example during a magnetic pulse, the current flows in a direction that tends to preserve the magnetic field (e.g., Lenz's Law).

In the context of electrical stimulation of the anatomy, certain parts of the anatomy (e.g., nerves, tissue, muscle, brain) act as a conductor and carry electric current when an electric field is presented. The electric field may be presented to these parts of the anatomy transcutaneously by applying a time varying (e.g., pulsed) magnetic field to the portion of the body. For example, in the context of TMS, a time-varying magnetic field may be applied across the skull to create an electric field in the brain tissue, which produces a current. If the induced current is of sufficient density, neuron membrane potential may be reduced to the extent that the membrane sodium channels open and an action potential response is created. An impulse of current is then propagated along the axon membrane which transmits information to other neurons via modulation of neurotransmitters. Such magnetic stimulation has been shown to acutely affect glucose metabolism and local blood flow in cortical tissue. In the case of major depressive disorder, neurotransmitter dysregulation and abnormal glucose metabolism in the prefrontal cortex and the connected limbic structures may be a likely pathophysiology. Repeated application of magnetic stimulation to the prefrontal cortex may produce chronic changes in neurotransmitter concentrations and metabolism so that depression is alleviated.

Before beginning a therapeutic and/or diagnostic procedure on a human subject, the size and the shape of the human subject's head may be determined. This determination may be made in order to properly determine where and how the procedure is to be performed on the specific human subject.

Since each human subject's head size and shape may be unique and since the margin of error when determining these locations may be low, accurate means for determining the size and shape of the human subject's head may be a time consuming and delicate procedure. Further, replicating theses determinations for each human subject and/or for each procedure for a human subject may be difficult. As such, the determination of the size and shape of the human subject's head may be performed one time before the first procedure for the human subject and saved for use during subsequent procedures.

FIG. 1 is a diagram of an example of a treatment system. The treatment system 100 may comprise a processor (not shown), a power supply (not shown), memory (not shown), a transceiver, (not shown), a treatment coil 102, an articulating arm 104, a display device 106, a sensor 110, and/or a human subject positioning apparatus 122. The treatment system 100 may be stationary or movable. For example, the treatment system 100 may be integrated into a movable cart, for example, as shown in FIG. 1. In one or more examples, the treatment system 100 may be a TMS treatment system (e.g., NeuroStar®) and/or any other therapeutic and/or diagnostic procedure system. The treatment coil 102 may be used to administer a therapeutic and/or diagnostic procedure to a human subject 120, for example, TMS. Although illustrated to include a treatment coil 102, the treatment system 100 may include any device for administration of therapeutic and/or diagnostic procedure of the human subject. The treatment system 100 may be used for a diagnostic procedure (e.g., solely for a diagnostic procedure).

The processor of the treatment system 100 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGAs) circuits, any other type of integrated circuit (IC), a state machine, and the like. The processor may perform signal coding, data processing, power control, input/output processing, and/or any other functionality that enables the treatment system 100 to operate. The processor may be integrated together with one or more other components of the treatment system 100 in an electronic package or chip.

The processor of the treatment system 100 may be coupled to and may receive user input data from and/or output user input data to the treatment coil 102, the articulating arm 104, the display device 106 (e.g., a liquid crystal display (LCD) display unit or organic light-emitting diode (OLED) display unit), the sensor 110, and/or the human subject positioning apparatus 122. The processor may access information from, and store data in, any type of suitable memory, such as non-removable memory and/or removable memory. The non-removable memory may include random-access memory (RAM), read-only memory (ROM), a hard disk, or any other type of memory storage device. The removable memory may include a subscriber identity module (SIM) card, a memory stick, a secure digital (SD) memory card, and the like. The processor may access information from, and store data in, memory that is not physically located within the treatment system 100, such as on a server (not shown).

The processor may receive power from the power supply, and may be configured to distribute and/or control the power to the other components in the treatment system 100. The power supply may be any suitable device for powering the treatment system 100.

The human subject 120 may be positioned within the human subject positioning apparatus 122. The human subject positioning apparatus 122 may be a chair, recliner, bed, stool, and/or the like. When performing treatment, the treatment coil 102 may be situated such that the human subject's head is positioned under the treatment coil 102. The treatment coil 102 may be adjusted by means of the articulating arm 104 and/or the like.

The treatment system 100 may comprise one or more computer software applications running on the processor. The computer software applications may provide a system graphical user interface (GUI) (e.g., a TMS system GUI) on the display device 106. The computer software applications may incorporate work flow management to guide a technician through the therapeutic and/or diagnostic procedure, and/or supervise and/or control one or more subsystems of the treatment system 100. For example, the computer software applications may control internal system functions, monitor the system status to ensure safe operation, and/or provide the user with a graphical means to manage the preparation for and/or the administration of the therapeutic and/or diagnostic procedure.

Interaction with the computer software applications may be provided via a user interface. In one or more embodiments, the user interface may be the display device 106, which may be a touch screen display. The display device 106 may include touch activated images of alphanumeric keys and/or buttons for user interaction with the treatment system 100. The display device 106 may provide graphic representations of the system activity, messages, and/or alarms. Interactive buttons, fields, and/or images may be displayed via the display device 106, and may enable the technician to direct and/or interact with system functions, for example, such as entering data, starting and stopping the procedure, running diagnostics, adjusting positioning and/or configuration of the treatment coil 102, adjusting the position of one or more sensor(s) (e.g., sensor 110), and/or the like.

The sensor 110 may comprise an infra-red (IR) sensor (e.g., IR camera), an ultrasonic transducer, an image sensor, a color sensor, a light sensor, a radio-frequency (RF) sensor, a tilt sensor, a microphone array, a laser scanner, and/or the like. Although illustrated as a fixed device, the sensor 110 may be mobile. The sensor 110 may communicate with the processor of the treatment system 100 via a wired interface (e.g., as shown) and/or wireless interface (e.g., radio frequency (RF) communication, such as, but not limited to WiFi®, Bluetooth®, LTE®, and/or the like). Although one sensor 110 is illustrated, the treatment system 100 may comprise more than one sensor 110.

The sensor 110 may be used to create a 2D and/or 3D digital reconstruction of the human subject's head, which for example, may include a fitted head model. For example, the sensor 110 may be used to determine one or more points (e.g., the cloud of points) associated with the human subject's head. The sensor 110 may be used to register one or more anatomical landmarks associated with the human subject's head. The sensor 110 may determine (e.g., capture) a cloud of points and/or perform anatomical landmark registration with or without the use of an indicator tool. The indicator tool may be a second sensor, the finger of the technician, an additional tool, etc. The sensor 110 may use an additional tool to assist in one or more of the procedures described herein. For example, the additional tool used by the treatment system 100 may include active and/or passive components to aid in detection by the sensor 110. For example, a reflector may be an example of a passive component/tool, while an LED may be an example of an active component/tool.

Figure 4:
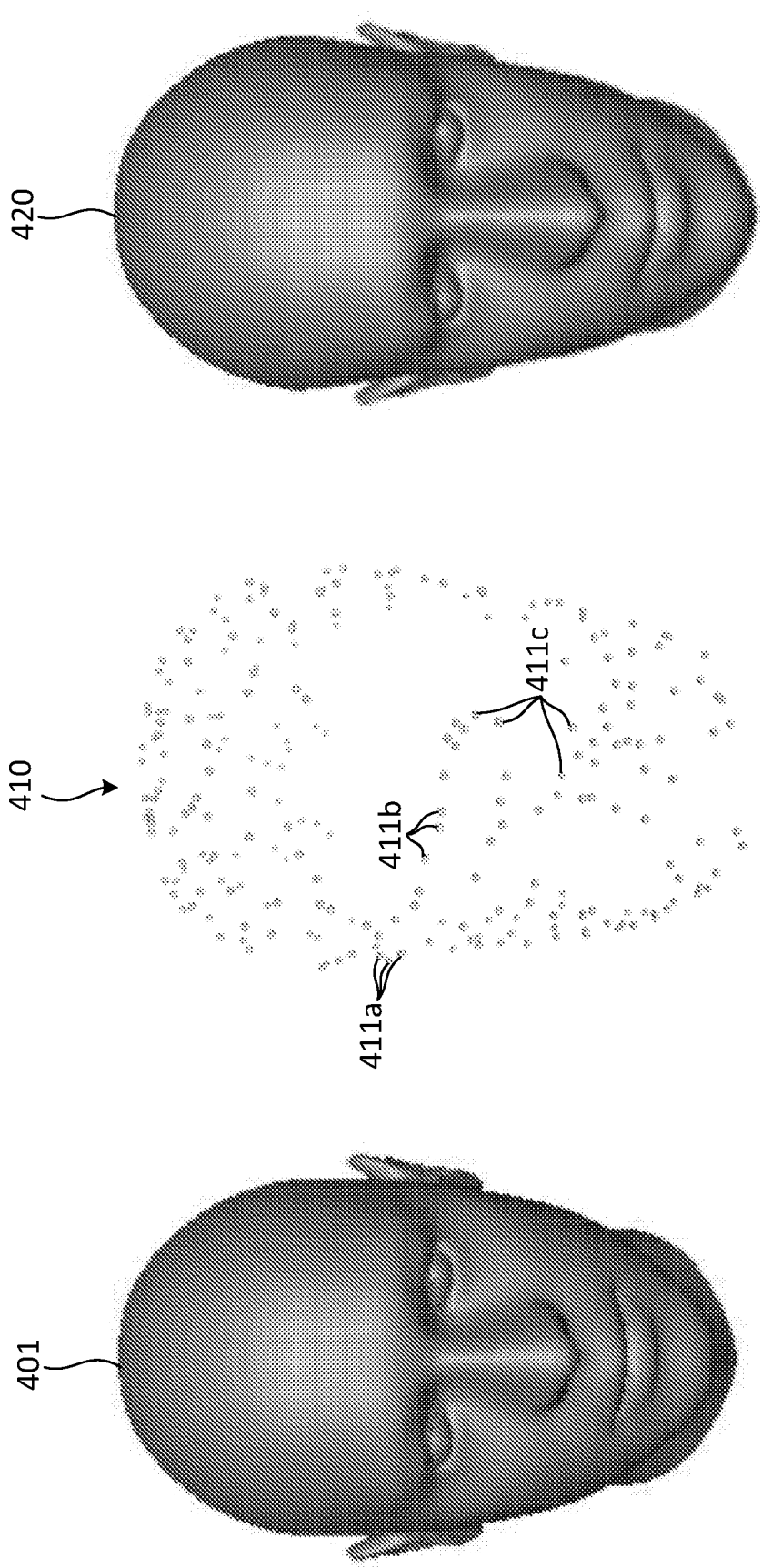
FIG. 4 is a diagram of an example of a predetermined head model, a point cloud, and a fitted head model.

The treatment system 100 may determine the size and/or shape of a human subject's head to generate a fitted head model, for example, a fitted head model of the human subject 120. The fitted head model may be a two dimensional (2D) or a three dimensional (3D) model. An example of a fitted head model is illustrated in FIG. 4. The fitted head model may be used to assist in a therapeutic and/or diagnostic procedure of the human subject 120. The treatment system 100 may store the fitted head model in memory. For example, the treatment system may use polygonal mesh (e.g., as a mathematical structure) to store the fitted head model.

The treatment system 100 may be used for any therapeutic and/or diagnostic procedure. For example, the treatment system may be used for TMS, tDCS, EEG, DBS, a diagnostic procedure, and/or the like. For example, the treatment system 100 may be used for any therapeutic and/or diagnostic procedure that includes the placement of electrodes, sensors, probes, and/or the like on a human subject, such as on the surface of a human subject's head. Although described with reference to a head model, the treatment system 100 may be configured to generate a model of any part of the human subject 120, such as, but not limited to, the arm, neck, chest, leg, and/or the like. The treatment system 100 may generate the fitted head model using the sensor 110.

Figure 2:
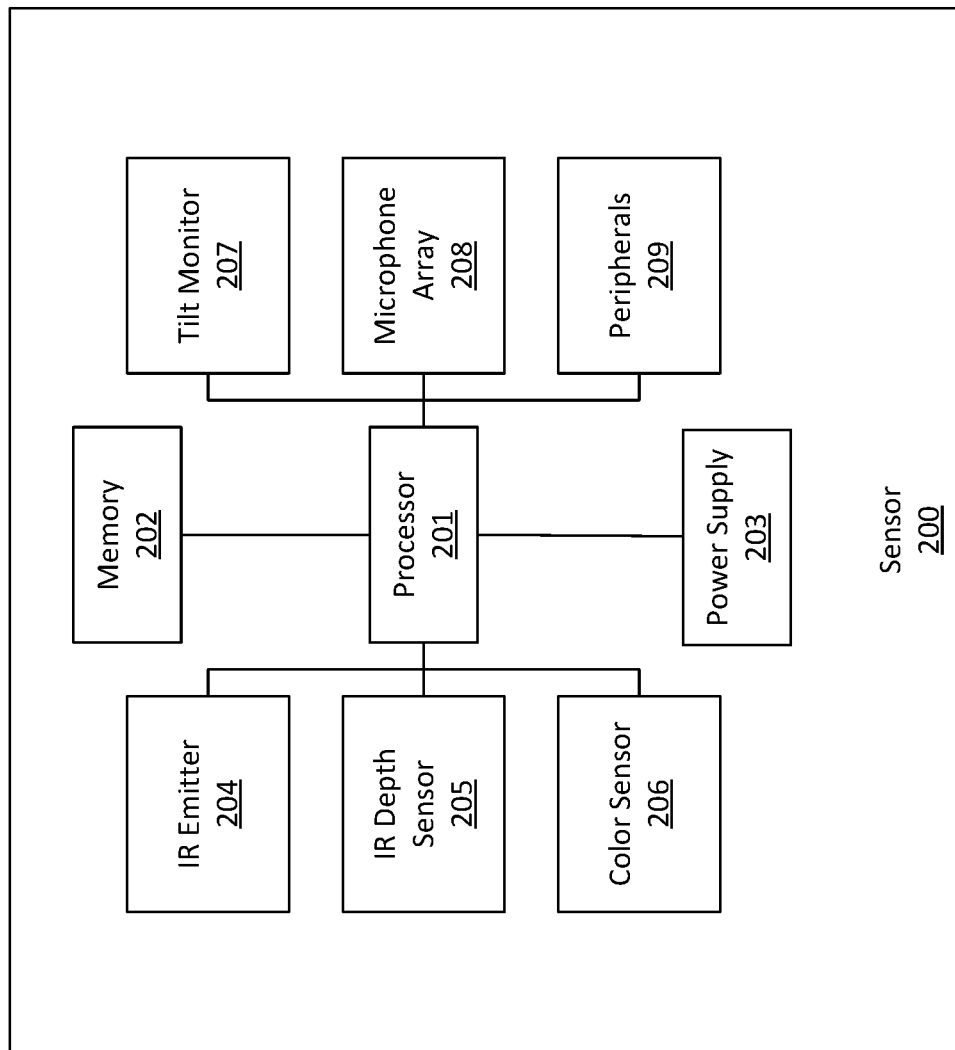
FIG. 2 is a diagram of an example of a sensor.

FIG. 2 is a diagram of an example of a sensor. The sensor 200 may be used with a treatment system (e.g., the treatment system 100). The sensor 220 may be an example of the sensor 110 of the treatment system 100. The sensor 200 may comprise a processor 201, memory 202, a power supply 203, an IR emitter 204, an IR depth sensor 205, a color sensor 206, a tilt monitor 207, a microphone array 208 (e.g., which may comprises one or more microphones), and/or other peripherals 209 (e.g., a transceiver). In an example, the sensor 200 may comprise the Kinect® system made by Microsoft® and/or an equivalent 3D IR depth sensing camera. The sensor 200 may include software that can be used to perform facial recognition, motion capture, video recording, and/or the like. The sensor 200 may include a user interface (e.g., a touch screen) and/or the sensor 200 may use the user interface (e.g., the display device 106) of the treatment system. The sensor 200 may be a fixed or mobile device. The sensor 200 may communicate with the processor of the treatment system 100 via a wired interface and/or a wireless interface.

The processor 201 of the sensor 200 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGAs) circuits, any other type of integrated circuit (IC), a state machine, and the like. The processor 201 may perform signal coding, data processing, power control, input/output processing, and/or any other functionality that enables the sensor 200 to operate. The processor 200 may be integrated together with one or more other components of the sensor 200 in an electronic package or chip. For example, the treatment system 100 and sensor 200 may share the same processor.

The processor 201 may be coupled to and may receive user input data from and/or output user input data to the memory 202, the power supply 203, the IR emitter 204, the IR depth sensor 205, the color sensor 206, the tilt monitor 207, the microphone array 208, and/or other peripherals 209. The processor 201 may access information from, and store data in, memory 202, such as non-removable memory and/or removable memory. The non-removable memory may include random-access memory (RAM), read-only memory (ROM), a hard disk, or any other type of memory storage device. The removable memory may include a subscriber identity module (SIM) card, a memory stick, a secure digital (SD) memory card, and the like. The processor 201 may access information from, and store data in, memory that is not physically located within the sensor 200, such as on the treatment system 100, on a server (not shown), etc.

The processor 201 may receive power from the power supply 203, and may be configured to distribute and/or control the power to the other components in the sensor 200. The power supply 203 may be any suitable device for powering the sensor 200.

Figure 3:
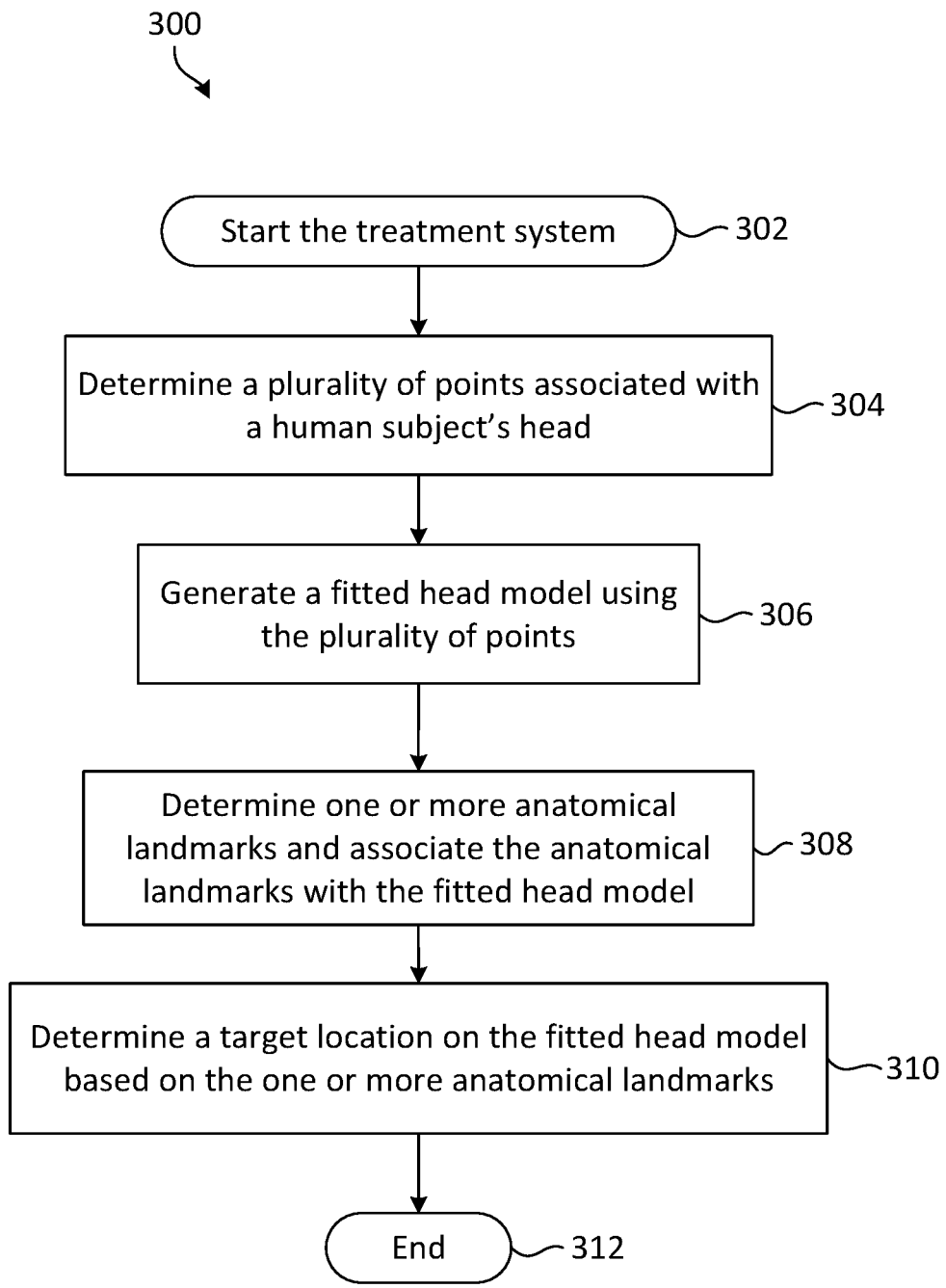
FIG. 3 is a flowchart of an example procedure for creating a fitted head model.

FIG. 3 is a diagram of an example procedure for creating a fitted head model. Although FIGS. 3-6 (e.g., the procedure 300) are described with reference to the treatment system 100, the procedure 300 may be performed by any system, for example, another therapeutic and/or diagnostic system. Further, although described with reference to a head model, the treatment system 100 may be configured to generate a model of any part of the human subject 120, such as, but not limited to, the arm, neck, chest, leg, and/or the like. In one or more embodiments, one or more of the processes (e.g., 302, 304, 306, 308, 310, and/or 312) of the procedure 300 may be omitted.

The treatment system 100 may be started at 302. At 304, the treatment system 100 may determine one or more points that are associated with the head of the human subject 120. The one or more points that are associated with the head of the human subject 120 may be referred to as a cloud of points or point cloud. The treatment system 100 may determine the point cloud using the sensor 110. The treatment system 100 may use the point cloud to generate a fitted head model, for example, as described herein. A point may be representative of a relative spatial location on the human subject's head. For example, a point (e.g., each point) of the cloud of points may comprise an x coordinate, a y coordinate, and a z coordinate in a coordinate system (e.g., Cartesian coordinate system, a cylindrical coordinate system, and/or the like). The treatment system 100 may use the sensor 110 to determine the relative location of a point (e.g., each point of the cloud of points) with respect to the sensor 110. The treatment system 100 may determine the cloud of points using the sensor 110 with or without the use of an additional tool, for example, as described herein.

The treatment system 100, via the sensor 110, may determine the relative location of the cloud of points without the use of an additional tool. The sensor 110 may capture one or more images of the human subject's head. For example, the sensor 110 may be placed in a scan mode and moved around the human subject's head. As the sensor 110 is moved, the sensor pose (e.g., the sensor's location and/or orientation) may be tracked and the sensor 110 may capture one or more views of the human subject's head. After collecting multiple views of the human subject's head in scan mode, the treatment system 100 may determine the pose of one or more captured frames and/or how a captured frame relates (e.g., is oriented) to other captured frames. The treatment system 100 may use the one or more images to determine the cloud of points.

The treatment system 100, via the sensor 110, may determine the relative location of the cloud of points using an additional tool, for example, an indicator tool. The indicator tool may be another sensor, a reflector, a fiducial, and/or other tool that the sensor 110 may use to determine the relative location of a point. The indicator tool may be used by a technician to indicate the location of the one or more points on the human subject's head. The treatment system 100 may determine the relative location of a point (e.g., each point of the cloud of points) with respect to the sensor by calculating the distance between the sensor 110 and the indicator tool. For example, the technician may touch the indicator tool to a particular point on a human subject's head. When the indicator tool is touching the point, the sensor 110 may detect the relative location of the indicator tool. For example, the indicator tool may send a signal (e.g., an IR transmission, an RF transmission, and/or the like) to the sensor 110. The signal may be a reflected signal that is redirected by the indicator tool back to the sensor 110 (e.g., a signal that originated at the sensor 110), sent directly from the indicator tool (e.g., originated at the indicator tool), and/or the like. The indicator tool may send the signal to the sensor 110 upon an instruction from the technician, for example, via the user interface of the treatment system.

A subset of the points of the cloud of points may comprise facial feature information. Facial feature information may include the location of one or more of the human subject's facial features. A facial feature may be, for example, the human subject's eye(s), nose, ear(s), mouth, chin, hairline, and/or the like. The treatment system 100 may determine that a subset of the points comprise facial feature information, for example, based on information provided from the sensor 110 and/or based on post-processing performed by the treatment system 100. For example, the sensor 110 may determine which points are relating to facial features of the human subject 120, and provide that information to the treatment system 100 along with the plurality of points. In one or more embodiments, the treatment system 100 may use the sensor 110 to determine the location of one or more facial features without the use of an additional tool. For example, the treatment system 100 may determine one or more facial features by capturing one or more images of the human subject's head using the sensor 110, and using recognition software to identify the facial features.

Figure 5:
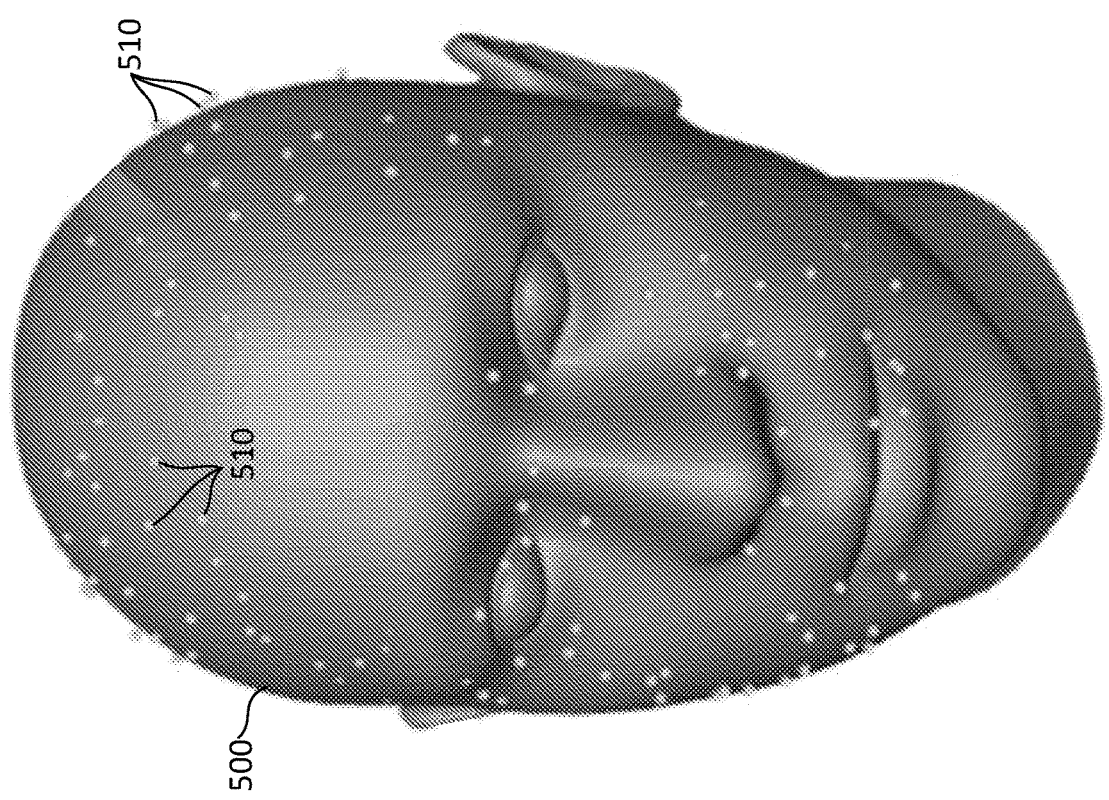
FIG. 5 is a diagram of an example of a predetermined head model superimposed with a plurality of points determined by a sensor.

At 306, the treatment system 100 may be configured to generate a fitted head model, which for example, may be referred to as head surface modeling. The treatment system 100 may generate the fitted head model using a predetermined head model and the plurality of points. The treatment system 100 may generate the fitted head model using a cubic spline method. The treatment system 100 may orient the predetermined head model to the plurality of points. The treatment system 100 may, for example, morph (e.g., stretch) the predetermined head model to the plurality of points to generate the fitted head model. FIGS. 4 and 5 may be used to describe examples of how the treatment system 100 may generate a fitted head model at 306. Upon creation, the fitted head model may be saved in memory and associated with the human subject 120, for example, so that it can be recalled and used for subsequent therapeutic and/or diagnostic procedures.

FIG. 4 is a diagram of an example of a predetermined head model, a point cloud, and a fitted head model. For example, the treatment system 100 may generate the fitted head model 420 using the predetermined head model 401 and the plurality of points 410. The predetermined head model 401 may be a generic head model that does not include any characteristics that are specific to one individual. A predetermined head model 410 may be used, for example, to keep the anonymity of the human subject 120, to provide information relating to one or more predefined coordinates, to reduce the total number of artifacts in the fitted head model, to reduce or eliminate the asymmetric nature or abnormal features of the human subject 120 (e.g., loss of ear, asymmetric bump, etc.), and/or the like.

The plurality of points 410 may comprise facial feature information 411*a-c*. The facial feature information 411*a-c* may include the relative location of one or more of the human subject's facial features. For example, the points 411*a* may comprise information relating to the relative location of the human subject's right ear, points 411*b* may comprise information relating to the relative location of the human subject's right eye, and points 411*c* may comprise information relating to the relative location of the human subject's nose. Although facial feature information relating to the human subject right ear, right eye, and nose are identified in the example in FIG. 4, it should be understood that more or less facial feature information may be provided by a point cloud.

FIG. 5 is a diagram of an example of a predetermined head model superimposed with a plurality of points determined by a sensor. The predetermined head model 500 may be an example of the predetermined head model 401. The plurality of points may be an example of the point cloud 410. The points 510 are a subset of the plurality of points that may be determined by a sensor (e.g., the sensor 110, sensor 200, and/or the like). It should be understood that not all points of the point cloud are labeled 510 for purposes of simplicity and clarity. As shown by the example of FIG. 5, some (e.g., all) of the points of the point cloud may not correspond directly with the predetermined head model 500. The treatment system 100 may generate the fitted head model using the predetermined head model 500 and the point cloud 510, for example, by morphing the predetermined head model 500 to the point cloud 510. As such, the fitted head model may have a similar look and feel as the predetermined head model 500, but to the dimensions of the point cloud 510 determined by the sensor.

Although not illustrated in the example in FIG. 4, the predetermined head 401 model may comprise predefined coordinates, for example, such as an EEG 10-20 coordinate grid, one or more treatment locations, and/or the like. The predetermined head model 401 may include location information relating to the one or more anatomical landmarks. An anatomical landmark may comprise a nasion, an inion, a lateral canthus, an external auditory meatus (e.g., ear attachment point), and/or one or more preauricular points of the human subject. An anatomical landmark may be associated with an x coordinate, a y coordinate, and a z coordinate of the predetermined head model 401.

The treatment system 100 may generate the fitted head model 420 using the predetermined head model 401 and the plurality of points 410. The fitted head model 420 may have a smooth surface. For example, the fitted head model 420 may have a smooth surface because it is created using a predetermined head model that also has a smooth surface. Further, in one or more embodiments, the treatment system 100 may determine that one or more points of the point cloud 410 are associated with rippling of the human subject's skin, loss of a facial feature, and/or an asymmetric lump, and generate the fitted head model 420 without the use of the these points. For example, the treatment system 100 may recognize an unusual fluctuation between points, an asymmetry between points on opposite sides of the head, and/or a variance between the points and that of the predetermined head mode 401, and determine that one or more points of the point cloud 410 are associated with rippling of the human subject's skin, loss of a facial feature, and/or an asymmetric lump. The treatment system 100 may not use these points when generating the fitted head model 420.

The fitted head model 420 may not include the human subject's hair. The treatment system 100 may identify, exclude, and/or remove the human subject's hair (e.g., facial hair and/or head hair) from the fitted head model 420. The hair may act as interference when generating the fitted head model 420. The exclusion of the human subject's hair may improve the accuracy when determining one or more target locations, for example, a MT location, a treatment location, and/or the like. The removal and/or exclusion of the human subject's hair from the fitted head model 420 may be performed by the treatment system 100 in one or more ways, which for example, may be performed in any combination.

The treatment system 100 may determine that one or more points of the point cloud 410 that are used to create the fitted head model 420 are associated with the human subject's hair. Thereafter, the treatment system 100 may generate the fitted head model 420 without the use of the points associated with the human subject's hair. For example, the treatment system 100 may use the human subject's facial features (e.g., those in close proximity to the hair in the front and/or back of the head) as a guide to determine the location of the hair, which for example, may be performed since the sensor's scan of the human patient may include the face of the human subject along with the rest of the human subject's head. The treatment system 100 may determine one or more location of the surface of the head under the hair using a probe (e.g., finger, tool, etc.) and use these locations to determine the location of the hair (e.g., the points in the point cloud that rest outside of these locations). The treatment system 100 may estimate the surface of the head under the hair using one or more facial features and/or anatomical landmarks. For example, removal of the hair may be performed by estimating intermediate points and using the intermediate points to map the head that is under the hair. The treatment system 100 may generate and use a mathematical head model using the known facial features and/or anatomical landmarks. A gel that is visible to the sensor 110 (e.g., detectible via IR) may be spread on the hair of the patient, such that the treatment system 100 may determine which of the plurality of points detected by the sensor 110 correspond to the human subject's hair and exclude those points when generating the fitted head model 420.

The plurality of points that are captured using the sensor 110 and used to create the fitted head model 420 may be devoid of information relating to the human subject's hair, such that the fitted head model 420 is devoid of information relating to the human subject's hair when it is generated by the treatment system 100. For example, the sensor 110 may comprise an IR sensor and the hair may not be recognized by the sensor 110. The sensor 110 may detect the warm (e.g., warmer) parts of the surface of the head under the hair through the hair and collect points that represent the surface of the head under the hair, but not the hair itself. A solution (e.g., liquid, gel, and/or the like) that is visible to the sensor 110 (e.g., detectible via IR) may be spread on the hair of the patient, such that the sensor 110 may detect the hair and exclude it from plurality of points that are used by the treatment system 100 to generate the fitted head model 420. The treatment system 100 may use an object (e.g., the TMS coil, the doctors hand, and/or the like) to compress the hair. For example, the object may be moved around the head, and the sensor 110 may recognize the object and determine the location of the surface of the head under the hair. The treatment system 100 may use a compression cap (e.g., swim cap) that is placed on the human subject's head to compress the hair to the surface of the head.

The treatment system 100 may generate the fitted head model 420 using the sensor 110 without the use of any additional tools. However, in one or more embodiments, the treatment system 100 may use one or more additional tools to generate the fitted head model 420. The additional tools may be used in conjunction with the sensor 110. The additional tools may include, but are not limited to, an indicator tool, a reflector, a fiducial, and/or the like, for example, as described herein.

Figure 6:
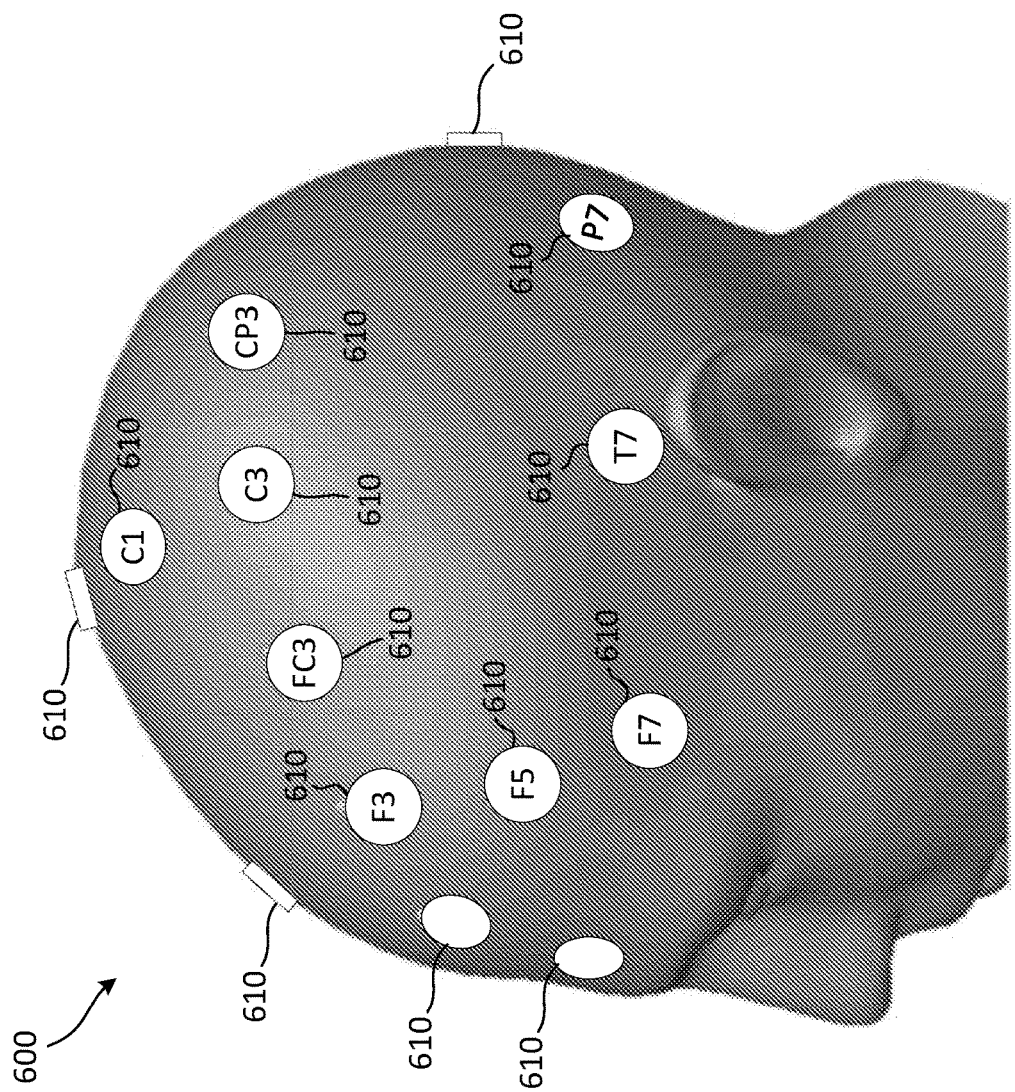
FIG. 6 is a diagram of an example fitted head model that includes an EEG 10-20 coordinate grid.

The fitted head model 420 may include one or more reference points, for example, such as predefined coordinate systems (e.g., an EEG 10-20 coordinate grid) that may be used for a therapeutic and/or diagnostic procedure, one or more target and/or treatment locations, and/or the like. FIG. 6 is a diagram of an example fitted head model that includes an EEG 10-20 coordinate grid. The fitted head model 600 may be an example of the fitted head model 420. The fitted head model 600 may comprise EEG 10-20 coordinate grid locations 610. The EEG 10-20 coordinate grid locations 610 may be used to determine one or more target locations and/or treatment locations. A target location (e.g., the motor threshold (MT) location) may be a reference point used to determine a treatment location. A treatment location may be used as the position for the treatment coil 102 for the diagnostic and/or therapeutic treatment, and/or the like.

The fitted head model 420 may include information relating to one or more facial features. For example, the facial feature information may be provided via the cloud of points 410. The facial feature information may be registered with the fitted head model 420. In one or more embodiments, the technician may identify and/or confirm a facial feature using a gesture, for example, by placing a finger on the facial feature. The treatment system 100 may determine the gesture using the sensor 110, for example, to identify that the technician's finger is on the facial feature. Once identified, the technician may confirm the facial feature via the user interface before the facial feature is registered with the fitted head model 420 by the treatment system 100.

At 308, the treatment system 100 may determine one or more anatomical landmarks and associate the anatomical landmarks on the fitted head model. This may be referred to as anatomical landmark registration. The treatment system 100 may determine one or more anatomical landmarks without the use of additional image information, such as MRI images, computer tomography (CT) images, an X-ray image, and/or the like. An anatomical landmark may comprise a nasion, an inion, a lateral canthus, an external auditory meatus (e.g., ear attachment point), and/or one or more preauricular points of the human subject 120. An anatomical landmark may be associated with an x coordinate, a y coordinate, and a z coordinate of the fitted head model. The treatment system 100 may register the anatomical landmarks with the fitted head model.

The treatment system 100 may determine the location of the anatomical landmarks using the facial feature information provided via the point cloud. For example, the treatment system 100 may perform triangulation and/or trilateration using the facial feature information (e.g., one or more points associated with the facial feature information) to determine the location of one or more anatomical landmarks of the human subject on the fitted head model. In one or more embodiments, the treatment system 100 may determine the location of the anatomical landmarks using the facial feature information provided via the point cloud if the predetermined head model does not include information relating to the anatomical landmarks The fitted head model may comprise the one or more anatomical landmarks when it is generated by the treatment system 100. For example, the treatment system 100 may integrate the anatomical landmarks from the predetermined head model into the fitted head model when created, for example, using the facial feature information as indicators of the specific location of the anatomical landmarks.

The treatment system 100 (e.g., using the sensor 100) may identify the anatomical landmarks and the technician may confirm the identification of the anatomical landmarks, for example, to associate the anatomical landmarks with the fitted head model. The technician may confirm the identification of the anatomical landmarks via the user interface of the treatment system 100.

The treatment system 100 may determine the anatomical landmarks using the sensor 110 with or without the use of an additional tool, such as an indicator tool. For example, the treatment system 100, via the use of an additional tool, may confirm the location of the anatomical landmarks after the fitted head model is created. For example, the technician may touch the additional tool to a particular location on a human subject's head. When the additional tool is touching the location, the sensor 110 may detect the relative location of the additional tool. For example, the additional tool may send a signal (e.g., an IR transmission, an RF transmission, and/or the like) to the sensor 110. The signal may be a reflected signal that is redirected by the indicator tool back to the sensor (e.g., originated at the sensor 110), sent directly from the additional tool (e.g., originated at the additional tool), and/or the like. The additional tool may send the signal to the sensor upon an instruction from the technician, for example, via the user interface of the treatment system 100.

Once associated with the fitted head model, the anatomical landmarks may be used to assist in the therapeutic and/or diagnostic procedure of the human subject. For example, the anatomical landmarks may be used to assist the technician in neuronavigation of the human subject's head. Further, the anatomical landmarks may be used to identify and/or store locations that may be used for therapeutic and/or diagnostic procedure, for example, the MT location and/or treatment location of the human subject. In one or more embodiments, anatomical landmark registration may be performed prior to the procedure (e.g., each procedure) for the human subject, for example, to orient the fitted head model with the human subject's actual head.

In one or more embodiments, the treatment system 100 may generate the fitted head model using the cloud of points without the use of a predefined head model. For example, the treatment system 100 may determine the cloud of points using a scan mode of the sensor, and may integrate one or more frames captured by the sensor to generate the fitted head model.

At 310, the treatment system 100 may determine one or more target locations on the fitted head model using the anatomical landmarks. A target location may be a treatment location or a reference point that is used to determine a treatment location, for example, the MT location and/or treatment location of the human subject 120. The treatment system 100 may determine a target location on the fitted head model based on one or more anatomical landmarks without the use of additional image information, for example, such as, but not limited to an MRI image, a CT image, and X-ray image, and/or the like.

The anatomical landmarks may be used to assist in neuronavigation of the human subject's head. For example, the treatment system 100 may display the fitted head model, the anatomical landmarks, and/or a target location on the display device, for example, to assist in a therapeutic or diagnostic procedure. For example, the treatment system 100 may perform TMS using the fitted head model and/or the target location. The treatment system 100 may save the fitted head model, along with the anatomical landmarks and/or target locations, for example, so that it can be recalled and used during a subsequent therapeutic or diagnostic procedure.

The treatment system 100 may include software that may perform neuronavigation, for example, to assist in the therapeutic and/or diagnostic procedure of the human subject. For example, the treatment system 100 may comprise software that may perform neuronavigation for TMS treatment. Neuronavigation may refer to the procedure by which the treatment system 100 allows for a technician to navigate in and/or around a head, a vertebral column, and/or other body part of a human subject, for example, before and/or during a procedure. For example, spatial information that may be part of the fitted head model may be used by the software for neuronavigation. The neuronavigation may be performed in real-time. The neuronavigation may track one or more objects, for example, simultaneously. As such, the treatment system 100 may be used to perform neuronavigation based on 3D IR object recognition and motion tracking.

Figure 7:
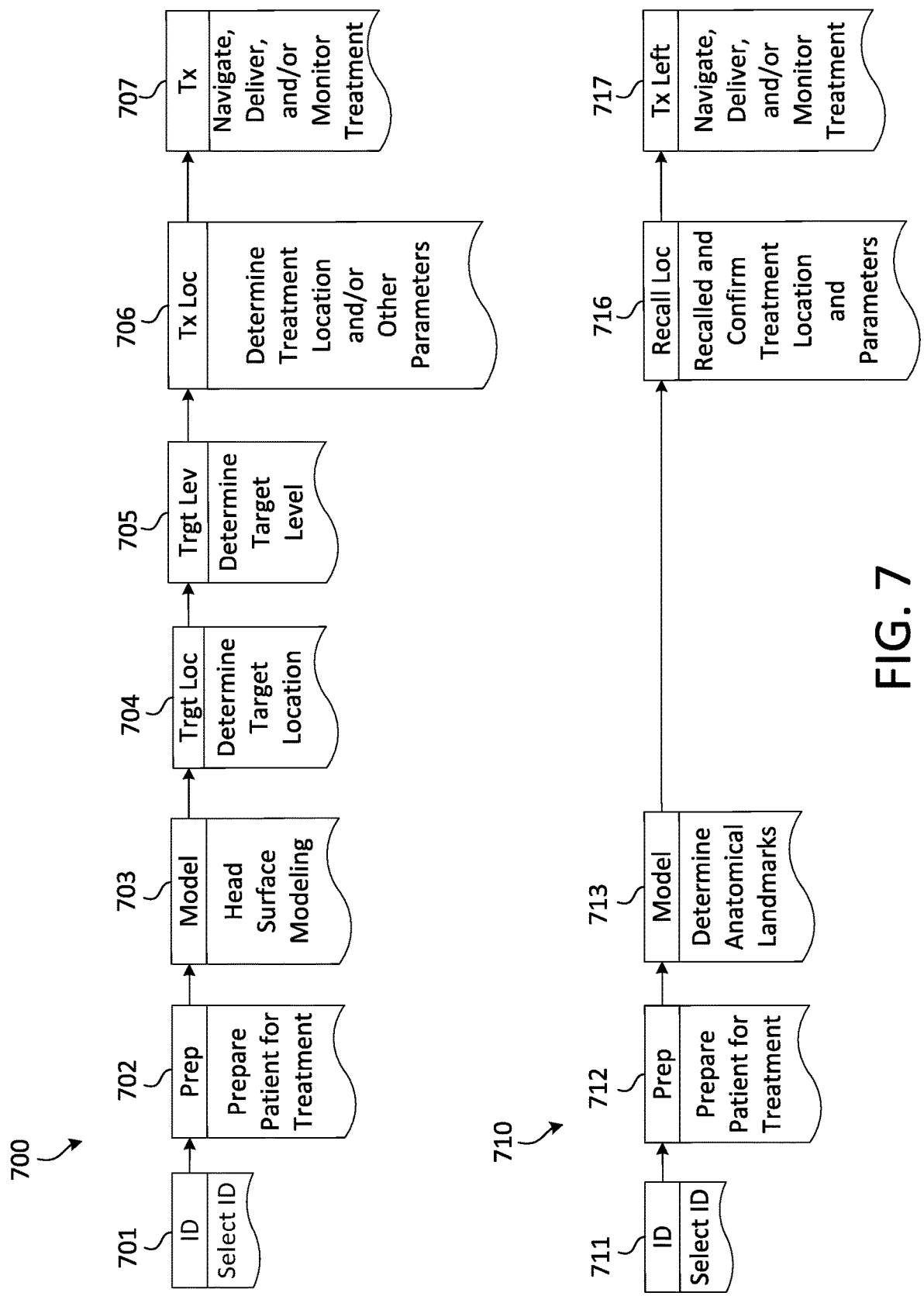
FIG. 7 is a diagram of example procedures for preparing for and/or performing a therapeutic and/or diagnostic procedure.

FIG. 7 is a diagram illustrating example procedures for preparing for and/or performing a therapeutic and/or diagnostic procedure. The procedures 700, 710 may be performed by a treatment system (e.g., the treatment system 100) and/or one or more sensors (e.g., sensor 110, sensor 200, and/or the like). Procedure 700 may be performed during the human subject's first visit, while procedure 710 may be performed during a subsequent, repeat visit. In one or more embodiments, one or more of the processes (e.g., 701-707 and 711-717) of the procedures 700, 710 may be omitted. For example, processes 704, 705 may be omitted from the procedure 700.

At 701, the treatment system may determine an identification (ID) (e.g., patient ID) for the human subject (e.g., via technician selection). The ID may be an alphanumeric that uniquely identifies the human subject. At 702, the human subject may be prepared for the therapeutic and/or diagnostic procedure. This may include positioning the human subject positioning apparatus, positioning a treatment coil with respect to the human subject, positioning one or more sensors with respect to the human subject's head, and/or positioning the human subject in the proper orientation. The sensor may be used to assist in the positioning of the human subject with respect to the one or more other objects (e.g., a treatment coil, additional tool, and/or other therapeutic and/or diagnostic tool). For example, the sensor may track the relative location of an object with respect to the human subject. The treatment system may indicate that the object is in the proper position by signaling to the technician, by displaying the relative position of the object and human subject on the display device, and/or the like.

At 703, the treatment system may generate a fitted head model. For example, the treatment system may generate the fitted head model in accordance with one or more of the embodiments described with reference to FIG. 3. The treatment system may determine a cloud of points using at least one sensor, and for example, without the use of an indicator tool. The cloud of points may comprise facial feature information. A facial feature may include, but is not limited to, a nose, an eye, an ear, a chin, hairline, and/or a mouth of the human subject. Facial feature information may include information relating to a relative location of one or more facial features of the human subject. The sensor may determine the relative location of one or more points (e.g., each point of the cloud of points) with respect to the sensor, and feed this information back to the treatment system. After the cloud of points is determined using the sensor, the cloud of points may be stored by the treatment system and/or used for generating the fitted head model.

The treatment system may generate the fitted head model using the cloud of points, for example, using a cubic spline method and/or the like. For example, the treatment system may use the cloud of points to morph (e.g., scale) a predefined head model to generate the fitted head model. The treatment system may generate the fitted head model using the cloud of points without the use of a predefined head model. For example, the treatment system may determine the cloud of points using a scan mode of the sensor, and may integrate one or more frames captured by the sensor to generate the fitted head model. As such, the treatment system may map the cloud of points to generate the fitted head model, morph a predetermined head model using the cloud of points to generate the fitted head model, integrate a plurality of captured frames to generate the fitted head model, and/or the like.

In one or more embodiments, the predetermined head model may include information relating to one or more reference points, such as, but not limited to a standardized set of reference points, such as, an EEG 10-20 coordinate grid, for example. The treatment system may generate a fitted head model that includes an overlaid reference grid (e.g., as shown in FIG. 6). For example, the reference points may be integrated into the fitted head model when generated. The reference grid may be used to assist the technician in locating a target location.

The fitted head model may have a smooth surface. The treatment system may generate the fitted head model without the human subject's hair, for example, as described herein. In one or more embodiments, the treatment system may determine that one or more points of the point cloud are associated with rippling of the human subject's skin, loss of a facial feature, an asymmetric lump, and/or the like, and generate the fitted head model without the use of the points associated with the rippling of the human subject's skin, loss of a facial feature, asymmetric lump, and/or the like.

The treatment system may determine the location of one or more anatomical landmarks on the fitted head model, for example, using the facial feature information. The treatment system may determine the location of the anatomical landmarks without the use of additional image information, such as, an MRI image, a CT image, an X-ray image, and/or the like. The treatment system may associate the anatomical landmarks with the fitted head model. An anatomical landmark may comprise a nasion, an inion, a lateral canthus, an external auditory meatus (e.g., ear attachment point), a preauricular point, and/or the like. In one or more embodiments, the treatment system may integrate the anatomical landmarks from the predetermined head model into the fitted head model when created, for example, using the facial feature information as indicators of the specific location of the anatomical landmarks. The treatment system may determine the location of the anatomical landmarks using the facial feature information provided via the point cloud, for example, if the predetermined head model does not include information relating to the anatomical landmarks.

At 704, the treatment system may determine a target location, for example, based on one or more anatomical landmarks and/or one or more reference points. The target location may be a treatment location or a reference point that is used to determine the treatment location. In one or more embodiments, the target location pay be the human subject's motor threshold (MT) location. Example methods of determining a human subject's MT location and/or treatment location may be described in U.S. Patent Application Publication No. 2009/0227830 A1, the contents of which are incorporated herein by reference. The target location may be stored in memory, for example, in association with the fitted head model. For example, the target location may be indicated by an icon on the fitted head model and may be used to assist in the therapeutic and/or diagnostic procedure of the human subject.

The human subject's head may be displayed with one or more reference points (e.g., a standardized set of reference points, such as, an EEG 10-20 coordinate grid), which may be used for determining the location of a target location. For example, the human subject's head and/or the fitted head model may be displayed on a display device (e.g., the display device 106) and, for example, a grid of reference points may be displayed (e.g., as shown in FIG. 6). For example, the reference points may be overlapped on the human subject's head image and/or fitted head model. The grid of reference points may be used to assist in the determination of the human subject's MT location and/or treatment location, for example, with or without the use of the indicator tool. The treatment system may determine and store the treatment location, the MT location, and/or other targets on the fitted head model, for example, to assist in a therapeutic and/or diagnostic procedure. For example, in TMS, the treatment system may use the human subject's MT location and/or the human subject's treatment location when performing treatment. The human subject's MT location and/or treatment location may be displayed with the fitted head model on the display device when calibrating and/or performing the therapeutic and/or diagnostic procedure.

After determining a target location of the human subject, the treatment system may determine a target location level for the human subject at 705. The target location level may include an amount (e.g., intensity) and/or duration at which an application of a procedure should be performed at the target location for the human subject, for example, to ensure that the target location is correct. For example, if the target location is the MT of the human subject, the MT level may include the strength of the pulse(s) that are applied to the human subject's MT location to induce a thumb twitch. The thumb twitch may indicate that the target location is on the human subject's motor strip. The human subject's target location level may be stored. For example, the human subject's MT level may be stored in association with the fitted head model, for example, by means of an MT level icon.

The human subject's treatment location may be determined at 706, for example, using the human subject's MT location as a guide. For example, the human subject's treatment location may be determined by moving the treatment tool (e.g., coil) from the MT location along a line in the anterior direction a prescribed distance (e.g., 5 cm). The resultant location may be the human subject's treatment location. The human subject's treatment location may be stored, for example, in association with the fitted head model. For example, the human subject's treatment location may be indicated by an icon that is different than the icon indicating the human subject's MT location. As such, the treatment system may determine the desirable placement location of a therapeutic and/or diagnostic device (e.g., a treatment coil, electrode, a sensor, and/or the like) for the therapeutic/diagnostic procedure of the human subject.

The treatment system may determine a treatment level for the human subject at 706. The treatment level may include an amount (e.g., intensity) and/or duration at which an application of the therapeutic and/or diagnostic procedure should be performed at the treatment location for the human subject.

After the human subject's treatment location is determined and stored, the fitted head model may be used to assist in the therapeutic and/or diagnostic procedure of the human subject. The fitted head model may include visual aids, for example, anatomical landmarks, reference points (e.g., a standardized set of reference points), marking of the human subject's motor threshold (MT) location, marking of the human subject's treatment location, and/or the like. The visual aids may assist a technician to setup and/or perform the therapeutic and/or diagnostic procedure of the human subject. Therapeutic and/or diagnostic procedure may be performed at 707. This may include further refinements of the treatment location during the therapeutic and/or diagnostic procedure. In one or more embodiments, the treatment may comprise TMS.

The treatment system may, for example, track of one or more objects, for example, before and/or during a treatment procedure. For example, the treatment system 100 may use one or more sensors to perform object tracking. The sensor may track the relative location of one or more objects, for example, with respect to other objects, and provide such information to the treatment system 100. The object may include an additional tool, a treatment and/or procedure device (e.g., the treatment coil 102), a human subject's head, one or more sensors, and/or the like. For example, the treatment system 100 may use object tracking to assist in navigating the treatment device (e.g., the treatment coil 102) to the treatment location of the human subject. Further, the treatment system 100 may use object tracking during the treatment procedure, for example, as described herein. Object tracking may be performed with or without the use of an additional tool (e.g., a fiducial).

The treatment system may track objects by attaching an additional tool (e.g., a reflector, a fiducial, and/or the like) on the treatment coil. The treatment system may track objects without the use of an additional tool. For example, the sensor may capture one or more images (e.g., in scan mode) to track the location of one or more objects, for example, with the use of recognition software. The treatment system may track objects to assist in navigating the treatment coil 102 to the treatment location of the human subject. Further, the treatment system may use object tracking during the treatment procedure.

During a therapeutic and/or diagnostic procedure, for example, the treatment and/or procedure device may be in close proximity to the human subject's head. The treatment and/or procedure device may be moved from one location to the other, for example, when performing the search for the human subject's MT location and/or when performing the procedure itself. The location of the treatment and/or procedure device may be tracked by the sensor to ensure it does not adversely affect the readings of the sensor. Further, the indicator tool may be attached to the human subject's head to more accurately capture the size and shape of the head, for example, to compensate for the movement of the human subject's head while capturing the cloud of points and/or the anatomical landmark registration.

Procedure 710 may be performed during a subsequent, repeat visit of a human subject. As such, the treatment system may have a fitted head model stored in memory. Procedure 710 may begin with the technician selecting the ID for the human subject at 711. The ID may have already been stored and associated with the human subject during a previous visit. As such, upon selecting the ID, the fitted head model, the treatment location, and/or the like may be uploaded and displayed by the treatment system. At 712, the human subject may be prepared for the therapeutic and/or diagnostic procedure (e.g., which may be substantially similar to 702).

At 713, the anatomical landmarks may be determined. Since the fitted head model may have been created and stored during a previous visit, the technician may register (e.g., only register) the anatomical landmarks of the human subject. For example, the technician may confirm the location of the anatomical landmarks on the fitted head model, for example, with or without the use of an indicator tool. The location of the anatomical landmarks may be confirmed prior to the procedure (e.g., each procedure) for the human subject, for example, to orient the fitted head model with the human subject's actual head. Procedure 710 may not include the determination of the MT location and/or treatment location of the human subject, for example, since this information may have already been created and stored during a previous visit. At 716, the treatment location and parameters may be recalled from memory and/or displayed for the technician (e.g., which may be substantially similar to 706). At 717, the therapeutic and/or diagnostic procedure may be administered to the human subject (e.g., which may be substantially similar to 707).

One or more of the following, in any combination, may be performed by a treatment system (e.g., the treatment system 100).

The sensor may measure and/or report (e.g., continuously measure and/or report) the relative position of one or more objects (e.g., tools, the human subject, etc.) for display (e.g., real-time display) to the technician. For example, the sensor may measure the relative location of a treatment tool (e.g., a coil) with respect to the human subject's head. The sensor may determine the location of the treatment coil that is in contact with the human subject's head (e.g., which portion(s) of the treatment tool are in contact with the head). The treatment system may use treatment tool's location information to determine if procedure is being performed properly. For example, for TMS, if the treatment coil falls outside of a predefined range with respect to the human subject's head (e.g., is too far or too close to the human subject's head), then the treatment system may alter or stop the therapeutic and/or diagnostic procedure.

The treatment system may use the sensor to calibrate a therapeutic and/or diagnostic procedure. For example, the treatment system may use human subject recognition software to determine the human subject, the patient ID, type of tool (e.g., coil type), and/or the parameters of the therapeutic and/or diagnostic procedure for the human subject based on the feedback from the sensor.

The treatment system may use voice commands to activate and/or manage setup of a therapeutic and/or diagnostic procedure (e.g., identification of anatomical landmarks) and/or the procedure itself. For example, the sensor may be used to relay voice commands to the treatment system.

The treatment system may use the sensor to recognize a tool, a human subject, a logo (e.g., a logo on a tool), and/or the like. The treatment system may authenticate a tool and/or a human subject based on its recognition via the sensor. For example, if the treatment system recognizes a tool, then the treatment system may allow for treatment of the human subject to occur. However, if the treatment system does not recognize the tool (e.g., if the tool is a sham tool, such as a sham coil, for example), then the treatment system may prevent the application of procedure to the human subject and/or log such activity. The treatment system may recognize and/or authenticate a tool based on the size of the tool, the shape of the tool, a logo on the tool, invisible IR ink on the tool, sound of the tool, a reflector on the tool, and/or the like. Recognition of a tool may be used for security and/or safety precautions. The recognition of a tool may be used for calibration of the therapeutic and/or diagnostic procedure. For example, the treatment system may calibrate the procedure differently based on the coil type detected via the sensor. The treatment system may verify that setup is accurate by recognizing one or more tools.

The treatment system may use the sensor to determine whether the human subject is experiencing a seizure. For example, the treatment system and/or the sensor may be calibrated with one or more parameters associated with a signature of a seizure (e.g., shaking of the human subject in excess of a predetermined amount, etc.). Upon detecting a seizure, the treatment system may adjust or stop the procedure for the human subject.

The sensor may be incorporated into augmented reality (AR) goggles. For example, the technician may wear the AR goggles. The technician may walk around the human subject while wearing the AR goggles to determine the cloud of points that the treatment system may use to generate the fitted head model. The display from the display device of the treatment system may be reproduced in AR googles, for example, to assist the technician in the preparation for the procedure and/or during the procedure.

The treatment system may use the sensor to detect the temperature of a tool that is used during a therapeutic and/or diagnostic procedure. For example, the treatment system, via the sensor, may detect the temperature of a coil used for TMS (e.g., using IR). If the treatment system determines that the temperature of the coil falls outside of a predetermined range (e.g., gets too hot or too cold), then the treatment system may adjust or stop the therapeutic and/or diagnostic procedure. This may be performed to ensure the safety of the human subject.

The treatment system may use the sensor to perform eye tracking. For example, the sensor may track the human subject's eyes for diagnostic purposes, for example, to determine whether the procedure is working (e.g., which the human subject is depressed and/or happy), whether the human subject is awake/asleep, and/or the like.

The treatment system may use the sensor to detect invisible IR ink, for example, to prevent reuse of a disposable tool. For example, the s treatment system, via the sensor, may read a unique alphanumeric on a disposable tool and cross-reference the alphanumeric with a listing of previously used alphanumerics. If the treatment system determines that the alphanumeric matches a previously used alphanumeric, then the treatment system may prevent the administration of the therapeutic and/or diagnostic procedure. This may be performed for safety, to track the number of administered procedures for a human subject and/or facility, to prevent the use of a counterfeit tool, and/or the like.

The treatment system may use the sensor to read a barcode. For example, prescriptions for a human subject may be sent to the procedure facility electronically using encrypted barcodes. The sensor may read the barcode, and upon authentication, enable the initiation of the therapeutic and/or diagnostic procedure to the human subject.

The treatment system may use the sensor to remotely monitor a procedure, for example, to ensure accurate calibration and/or safety. For example, the sensor may send a video (e.g., real-time streaming video) to a technician who may be at a remote location via the treatment system. The technician may watch the procedure (e.g., in real-time) to ensure that the procedure is being accurately and safely performed.

The treatment system, via the sensor, may use gesture controls to adjust and/or administer the therapeutic and/or diagnostic procedure to the human subject. For example, the treatment system may use the Natural User Interface (NUI) for gesture control. The gestures may be used to confirm the location of the human subject's MT. For example, the treatment system, using feedback from the sensor, may detect the twitch of the human subject's thumb upon the application a pulsing magnetic field to the human subject's MT location. The human subject's thumb may be fitted with an additional sensor, for example, to assist the detection of the twitch by the treatment system.

Although described with reference to the head of a human subject, one or more of the embodiments described herein may be applied to anatomies other than the head. For example, the treatment system may be used to create a fitted model of an arm, leg, hand, foot, chest, and/or other anatomy of a human subject. Further, the treatment system may be used to create a fitted model of an anatomy of a subject other than humans, such as birds, amphibians, reptiles, fish, insects, and/or other mammals.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A system for creating a digital three-dimensional re construction of a human subject's head, the system comprising:
   a treatment coil;
   a sensor; and
   a processor configured to:
      generate a fitted head model using a predetermined head model and feedback from the sensor without requiring the use of magnetic resonance imaging (MRI) image information, x-ray image information, or computer tomography (CT) image information of the human subject;
      determine a location of one or more anatomical landmarks on the fitted head model, the anatomical landmarks comprising one or more of a nasion, an inion, a lateral canthus, an external auditory meatus, or one or more preauricular points of the human subject;

determine a motor threshold location or a treatment location for the human subject on the fitted head model using the anatomical landmarks and the predetermined head model and without requiring the use of MRI information, x-ray image information, or CT image information of the human subject; and perform a transcranial magnetic stimulation (TMS) procedure based on the motor threshold location or the treatment location using the treatment coil.

2. The system of claim 1, wherein the processor is configured to:

determine a plurality of points associated with the human subject's head using the feedback from the sensor; and generate the fitted head model using the predetermined head model and the plurality of points associated with the human subject's head.

3. The system of claim 2, wherein the sensor is configured to capture one or more images of the human subject's head, and wherein the processor is configured to generate the fitted head model using the predetermined head model, the anatomical landmarks, the plurality of points associated with the human subject's head, and the one or more images of the human subject's head.

4. The system of claim 3, wherein the processor is configured to determine facial feature information based on the one or more images of the human subject's head; and wherein the processor is configured to determine the location of the one or more anatomical landmarks on the fitted head model using the facial feature information.

5. The system of claim 1, wherein the sensor comprises an infrared sensor.

6. The system of claim 2, wherein the processor is configured to determine the plurality of points using the feedback from the sensor and the use of an indicator tool, wherein the plurality of points comprise the one or more anatomical landmarks.

7. The system of claim 1, wherein the treatment location corresponds to an anatomical region within a human brain and is associated with a neuropsychiatric disorder.

8. The system of claim 1, wherein the sensor comprises an image sensor or a light sensor.

9. The system of claim 1, wherein the processor is further configured to:

monitor a position of the treatment coil using the sensor while performing TMS;

determine that the position of the treatment coil falls outside of a predefined range with respect to the human subject's head; and alter or stop performing TMS.

10. The system of claim 1, further comprising:

augmented reality (AR) goggles that comprise the sensor.

11. A system for creating a digital three-dimensional reconstruction of a human subject's head, the system comprising:

a treatment coil;

a sensor configured to determine a plurality of points associated with the human subject's head and capture one or more images of the human subject's head; and a processor configured to:

generate a fitted head model using a predetermined head model, the plurality of points associated with the human subject's head, and the one or more images of the human subject's head requiring the use of magnetic resonance imaging (MRI) image information, x-ray image information, or computer tomography (CT) image information of the human subject;

determine a location of one or more anatomical landmarks on the fitted head model, the anatomical landmarks comprising one or more of a nasion, an inion, a lateral canthus, an external auditory meatus, or one or more preauricular points of the human subject;

determine a motor threshold location or a treatment location for the human subject on the fitted head model using the anatomical landmarks and the predetermined head model and without requiring the use of MRI information, x-ray image information, or CT image information of the human subject; and perform a transcranial magnetic stimulation (TMS) procedure based on the motor threshold location or the treatment location using the treatment coil.

12. The system of claim 11, wherein the processor is configured to determine facial feature information based on the one or more images of the human subject's head.

13. The system of claim 11, wherein the system further comprises an indicator tool, and wherein the processor is configured to confirm the location of the one or more anatomical landmarks using the indicator tool.

14. The system of claim 11, wherein the predetermined head model comprises a predefined motor threshold location or a predefined treatment location.

15. The system of claim 11, wherein the sensor comprises an image sensor or a light sensor.

16. The system of claim 11, wherein the predetermined head model comprises a predefined motor threshold location or a predefined treatment location.

17. A method for creating a digital three-dimensional reconstruction of a human subject's head, the method comprising:

positioning a plurality of sensors with respect to the human subject's head;

generating a fitted head model using a predetermined head model and feedback from the plurality of sensors using the predetermined head model and without requiring the use of magnetic resonance imaging (MM) image information, x-ray image information, or computer tomography (CT) image information of the human subject;

determining a location of one or more anatomical landmarks on the fitted head model, the anatomical landmarks comprising one or more of a nasion, an inion, a lateral canthus, an external auditory meatus, or one or more preauricular points of the human subject;

determining a motor threshold location or a treatment location for the human subject on the fitted head model using the anatomical landmarks without requiring the use of MRI information, x-ray image information, or CT image information of the human subject;

determining parameters of a transcranial magnetic stimulation (TMS) procedure based on the feedback from the plurality of sensors; and performing the TMS procedure using the parameters based on the motor threshold location or the treatment location using a treatment coil.

18. The method of claim 17, further comprising:

monitoring, while performing TMS, a position of a TMS coil using the plurality of sensors;

determining that the TMS coil falls outside of a predefined range with respect to the human subject's head; and altering or stopping the performance of TMS.

19. The method of claim 17, further comprising:
determining a plurality of points associated with the human subject's head using the feedback from the plurality of sensors and an indicator tool; and
generating the fitted head model using the predetermined head model and the plurality of points associated with the human subject's head.

20. The method of claim 17, further comprising:
determining an identity of the human subject based on the feedback from the plurality of sensor; and
determining the parameters of the TMS procedure based on the identity of the human subject.

\* \* \* \* \*